(12) United States Patent
Smitt et al.

(10) Patent No.: US 8,393,788 B2
(45) Date of Patent: Mar. 12, 2013

(54) DIGITAL X-RAY IMAGE CAPTURING DEVICE

(75) Inventors: Asbjorn Smitt, Gibraltar (DK); Sung Woon Lee, Daejeon (KR)

(73) Assignee: 3D Imaging & Simulations Corp., Daejeon (KR)

( * ) Notice: Subject to any disclaimer, the term of this patent is extended or adjusted under 35 U.S.C. 154(b) by 0 days.

(21) Appl. No.: 12/738,318

(22) PCT Filed: Feb. 2, 2010

(86) PCT No.: PCT/KR2010/000634
§ 371 (c)(1),
(2), (4) Date: Apr. 16, 2010

(87) PCT Pub. No.: WO2011/074738
PCT Pub. Date: Jun. 23, 2011

(65) Prior Publication Data
US 2012/0243665 A1    Sep. 27, 2012

(30) Foreign Application Priority Data

Dec. 18, 2009 (KR) .................. 10-2009-0126645
Jan. 29, 2010 (KR) .................. 10-2010-0008615

(51) Int. Cl.
*G03B 42/04* (2006.01)
(52) U.S. Cl. ......... 378/182; 250/585; 250/588; 250/589
(58) Field of Classification Search .......... 378/181, 378/182; 250/580–590
See application file for complete search history.

(56) References Cited

U.S. PATENT DOCUMENTS 7,274,033 B2    9/2007    Yonekawa et al.
2010/0148096 A1*  6/2010   Neushul ............... 250/585

FOREIGN PATENT DOCUMENTS

KR    10-2008-0048052    5/2008
KR    10-2010-0021840    2/2010

* cited by examiner

*Primary Examiner* — Courtney Thomas
(74) *Attorney, Agent, or Firm* — Lexyoume IP Meister, PLLC.

(57) ABSTRACT

Disclosed is a digital X-ray image capturing device for easy mobility, including: a cassette having a built-in image plate; an image plate transfer device for taking the image plate out of the cassette and transferring the same to a scanning point; an image scanning device for scanning an X-ray latent image of the image plate by irradiating laser beams to the scanning point; an internal body including the image plate transfer device and the image scanning device; and an external housing surrounding the internal body. The image plate transfer device includes: a scan drum having a fastening means on a surface thereof, the fastening means being combined with an end of the image plate; at least one roller installed near the scan drum to closely wind the image plate on the surface of the scan drum; and an electric power means for applying torque to the scan drum. The slide mounting type or up-mounting type of cassette can be attached to the image plate transfer device.

20 Claims, 16 Drawing Sheets

DIGITAL X-RAY IMAGE CAPTURING DEVICE

TECHNICAL FIELD

The present invention relates to a compact digital X-ray image capturing device for convenient mobility.

BACKGROUND ART

In general, an X-ray image is acquired by developing an X-ray scanned film. When the X-ray image is captured from the film, films, a developer, a developing device, and a film storage bay as well as an X-ray device are additionally required. When the wrong photos are taken, additional materials for a retake are needed. Further, a user cannot immediately see the taken images since a predetermined time is spent to develop the film after X-ray shooting.

As a solution to such problems, computed radiography (CR) devices have been widely used. Computed radiography devices capture digital X-ray images by irradiating X-rays on an image plate instead of a film and scanning a latent image that is stored on the image plate by use of laser beams.

In detail, when the X-rays are irradiated on the image plate, a latent image that has energy proportional to the irradiated amount of X-rays is generated on the image plate. When the laser beams with the wavelength of red spectrum are irradiated on the image plate, the latent image is manifested with the wavelength of blue, and the manifested image is scanned to capture a digital X-ray image. The image plate is exposed to strong light to eliminate the remaining latent image, and the image plate is then used for subsequent photographing.

The above information disclosed in this Background section is only for enhancement of understanding of the background of the invention and therefore it may contain information that does not form the prior art that is already known in this country to a person of ordinary skill in the art.

DISCLOSURE

Technical Problem

When the conventional computed radiography device is used, the user must detach the cassette in which an image plate is built from the conventional computed radiography device, and he must move it to another scanner in order to scan the image after the image plate is exposed to the X-rays, and consecutive photo taking is impossible because of frequent attachment and detachment of the cassette.

Therefore, a method for installing the cassette into the computed radiography device can be considered in order to prevent frequent attachment/detachment of the cassette. However, since sufficient space is needed to transfer the image plate to the scanner, the volume of the computed radiography device must be increased. The computed radiography device has to be fixedly installed in a specific place.

Technical Solution

The present invention has been made in an effort to provide a digital X-ray image capturing device having advantages of eliminating the process of attaching or detaching a cassette with a built-in image plate.

The present invention has been made in another effort to provide a digital X-ray image capturing device having advantages of occupying less space while it has a built-in cassette and providing ease of mobility.

An exemplary embodiment of the present invention provides a digital X-ray image capturing device using a slide mounting type of cassette.

In detail, the digital X-ray image capturing device includes: a cassette having a built-in image plate; an image plate transfer device for taking the image plate out of the cassette and transferring the same to a scanning point; an image scanning device for scanning an X-ray latent image of the image plate by irradiating laser beams to the scanning point; an internal body including the image plate transfer device and the image scanning device; and an external housing surrounding the internal body.

The image plate transfer device includes: a scan drum having a fastening means on a surface thereof, the fastening means being combined with an end of the image plate; at least one roller installed near the scan drum to closely wind the image plate on the surface of the scan drum; and an electric power means for applying torque to the scan drum.

The fastening means formed on a surface of the scan drum is a latch groove, and a latch protrusion formed at an end of the image plate is combined with the latch groove.

An inserting groove for installing the cassette in the image plate transfer device is formed on the top of one side of the external housing.

Another embodiment of the present invention provides a digital X-ray image capturing device using an up-mounting type of cassette.

In detail, the digital X-ray image capturing device includes: a cassette having a built-in image plate; an image plate transfer device for taking the image plate out of the cassette and transferring the same to a scanning point; an image scanning device for scanning an X-ray latent image of the image plate by irradiating laser beams to the scanning point; an internal body including the image plate transfer device and the image scanning device; and an external housing surrounding the internal body.

The image plate transfer device includes: a scan drum having a fastening means on a surface thereof, the fastening means being combined with an end of the image plate; at least one roller installed near the scan drum to closely wind the image plate on the surface of the scan drum; and an electric power means for applying torque to the scan drum.

The fastening means formed on a surface of the scan drum is an installing groove, and an installing protrusion formed at an end of the image plate is combined with the installing groove.

A locking hole for fixing an end of the image plate to a surface of the scan drum is formed at both sides of an end of the image plate, and the scan drum further includes a locking means including a locking pin inserted into the locking hole of the image plate and fixing the image plate to the scan drum.

Advantageous Effects

According to embodiments of the present invention, when the cassette is attached, there is no need to detach the same so as to scan the image plate to thereby enabling continuous photographing, and mechanical abrasion caused by frequent attachment/detachment of cassette is minimized.

Also, according to exemplary embodiments of the present invention, free mobility is provided since the device occupies a lesser area while having a cassette therein.

BEST MODE

Figure 1:
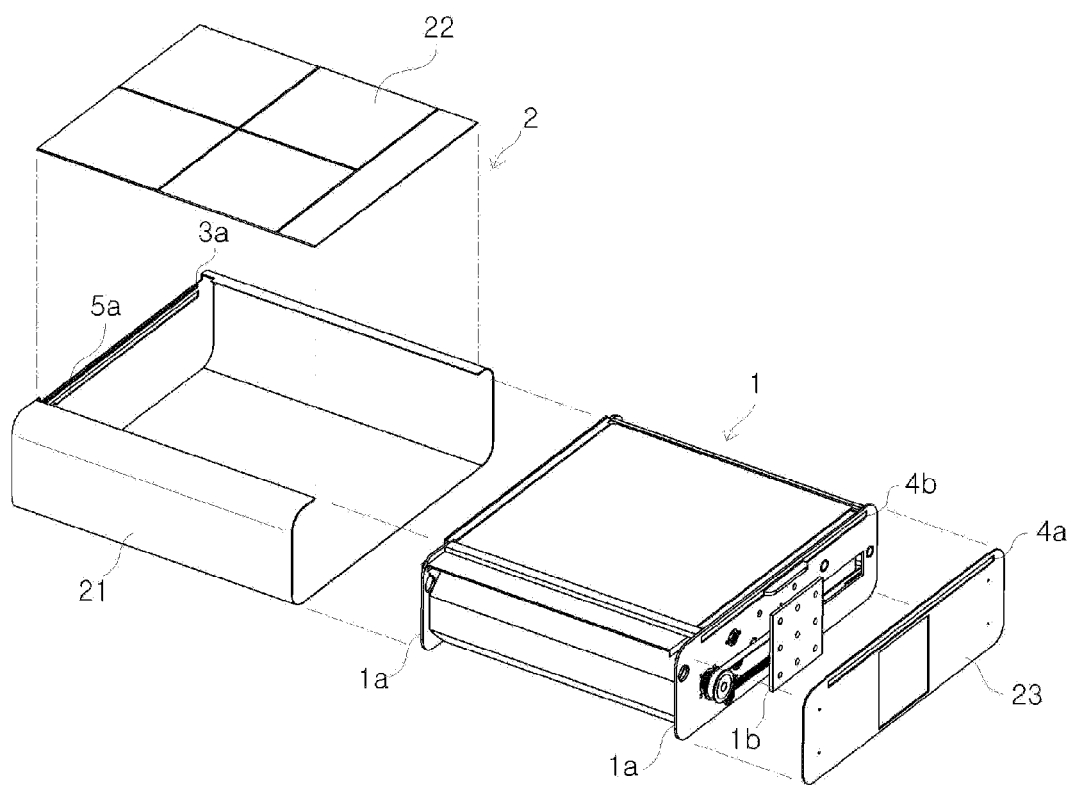
FIG. 1 shows an exploded perspective view of an X-ray image capturing device according to a first exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, unless explicitly described to the contrary, the word "comprise" and variations such as "comprises" or "comprising" will be understood to imply the inclusion of stated elements but not the exclusion of any other elements.

Preferred exemplary embodiments of the present invention will now be described in detail with reference to accompanying drawings.

A first exemplary embodiment discloses an X-ray image capturing device using a slide mounting type of cassette.

A user pushes a cassette in an insert hole provided at a side of the X-ray image capturing device so that a latch protrusion of an image plate built in the cassette may be accurately inserted into a latch groove of a scan drum. The above-noted cassette is called a slide mounting type of cassette.

FIG. 1 shows an exploded perspective view of an X-ray image capturing device according to a first exemplary embodiment of the present invention.

As shown in FIG. 1, the X-ray image capturing device includes an internal body 1 with a built-in image plate transfer device, an external housing 2 surrounding the internal body 1, a cassette 3 with a built-in image plate, an ion chamber 4, and a grid 5.

The ion chamber 4 senses a stored amount of X-ray energy that has passed through a subject, and notifies a controller 1000 of a time to stop irradiation of the X-rays. When the ion chamber 4 is used, there is no need to newly set an X-ray irradiation amount again depending on the size of the subject (or a photographing area) during the X-ray photographing process.

The grid 5 controls the X-ray image to look clearer by absorbing the energy that is scattered from the X-rays and accordingly preventing the energy from reaching the image plate 31.

The external housing 2 includes a case main body 21, a front plate 22 for protecting a top side of the internal body 1, and a side cover 23 for protecting a side of the internal body 1.

Side plates 1a for fixing an image plate transfer device are provided at both sides of the internal body 1, and an arm mount 1b for fixing the X-ray image capturing device to an X-ray bucky stand or an X-ray bucky table can be installed in at least one of the side plates 1a.

Figure 2:
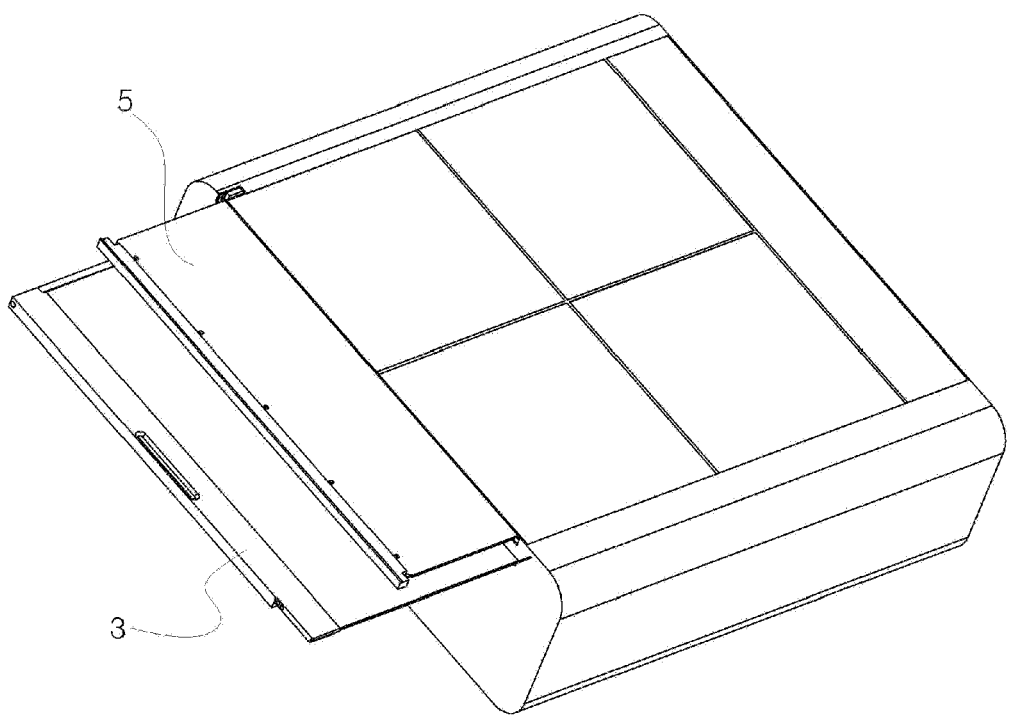
FIG. 2 shows a perspective view for installing a cassette and a grid in an image capturing device.
Figure 3:
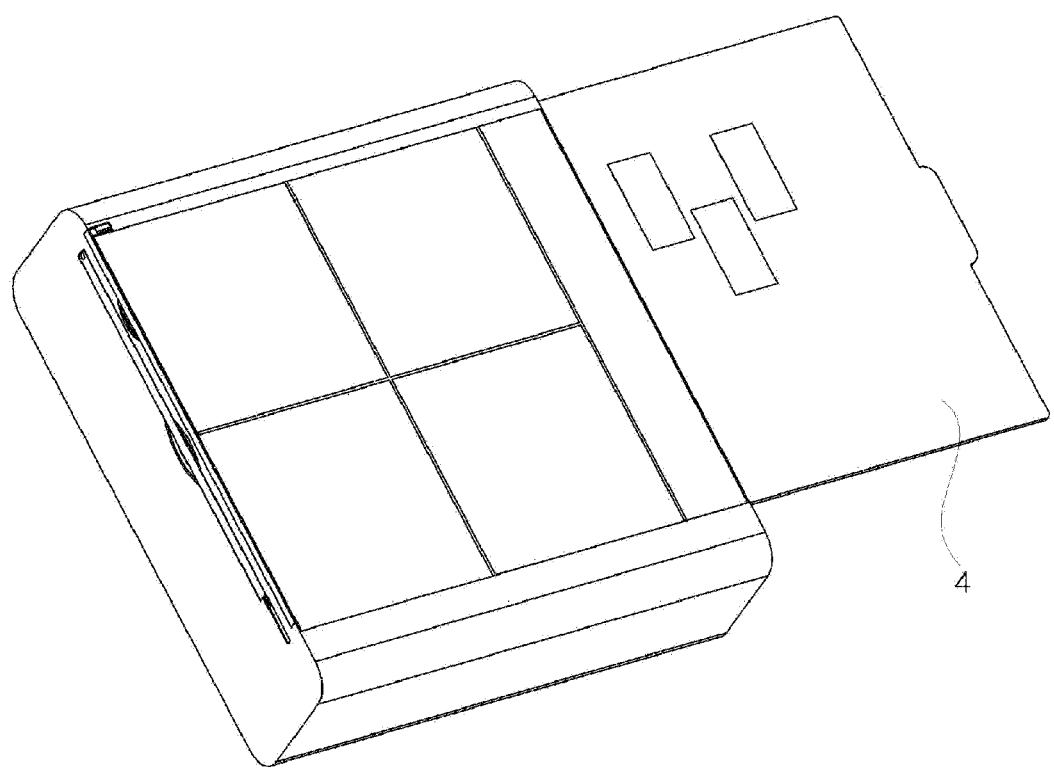
FIG. 3 shows a perspective view for installing an ion chamber in an image capturing device.

Insert holes 4a and 4b for installing the ion chamber 4 in the X-ray image capturing device are formed on the top of the side cover 23 and the top of the side plate 1a at the side of the side cover 23. Two insert holes 3a and 5a for installing the cassette 3 and the grid 5 are respectively formed on the case main body 21 at the opposite side of the side cover 23 and the top of the side plate 1a. FIG. 2 shows a perspective view for installing a cassette 3 and a grid 5 in an image capturing device, and FIG. 3 shows a perspective view for installing an ion chamber 4 in an image capturing device.

A configuration of the internal body 1 will be described in detail with reference to FIG. 4 and FIG. 5.

Figure 4:
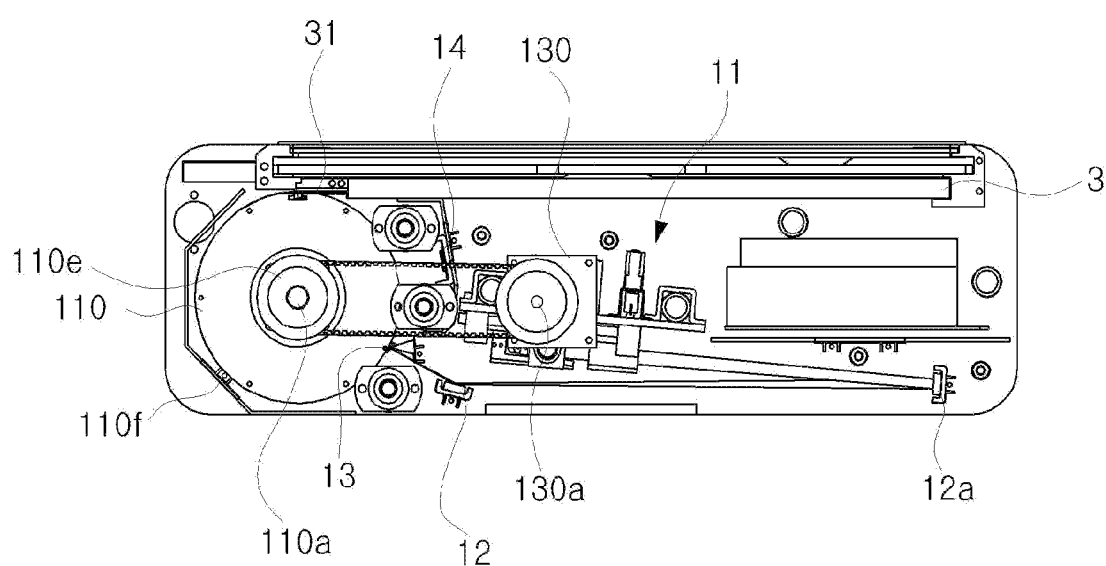
FIG. 4 shows a side view of a state in which a side plate is removed from an internal body of FIG. 1.
Figure 5:
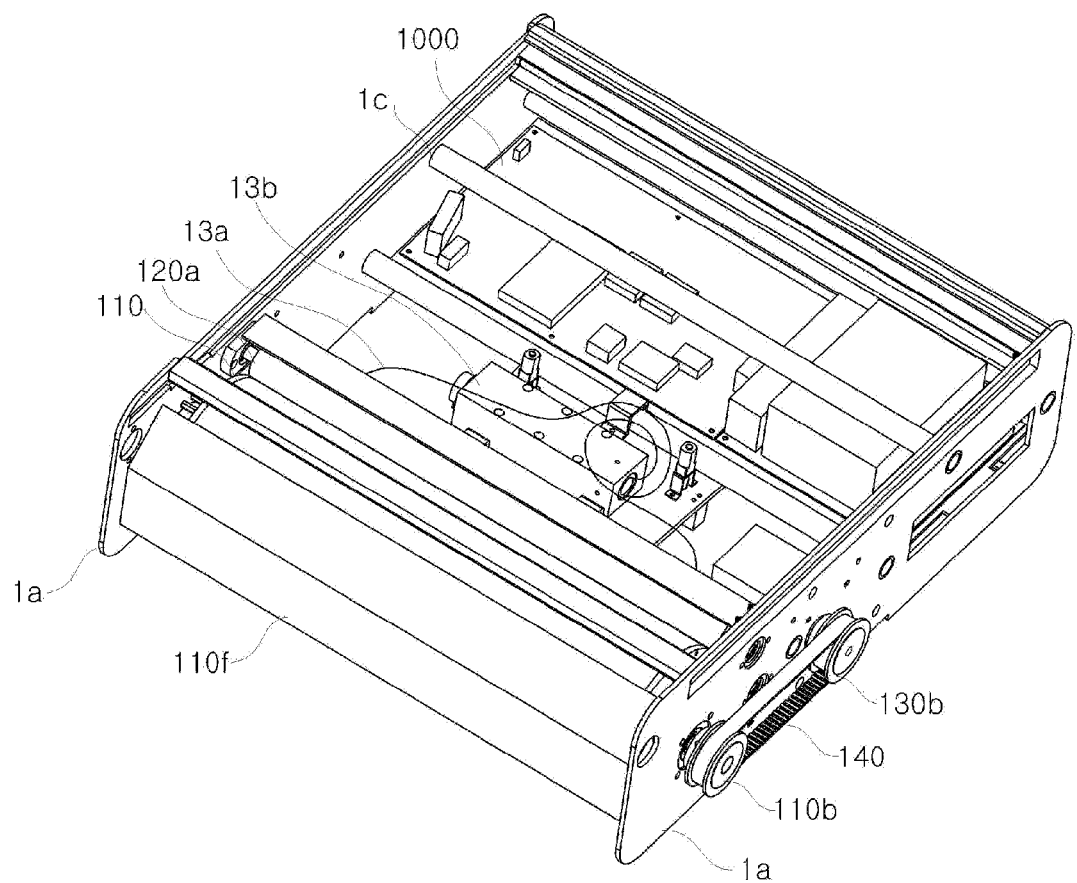
FIG. 5 shows a perspective view of a state in which a cassette is removed from an internal body of FIG. 1.

FIG. 4 shows a side view of a state in which a side plate 1a is removed from the internal body 1 of FIG. 1, and FIG. 5 shows a perspective view of a state in which a cassette 3 is removed from the internal body 1 of FIG. 1.

The internal body 1 includes an image scanning device, an image plate transfer device, and the controller 1000. As shown in FIG. 4 and FIG. 5, the image scanning device, the image plate transfer device, and the controller 1000 are fixed to the internal body 1 by at least one support plate (or a panel or board). A gap between the side plates 1a is maintained at a constant amount by at least one supporter 1c disposed in the horizontal direction with respect to the internal body 1.

First, the image scanning device will be described.

In FIG. 4, the image scanning device includes a laser beam scanner 11, one or more reflection mirrors 12a-12b for controlling a progress angle of the laser beams to irradiate the laser beams to a predetermined scanning point 13, and a scanner for scanning an X-ray latent image of the image plate 31, and it can further include an eraser 14 for erasing an X-ray latent image by exposing the image plate 31 to strong light.

A configuration of the laser beam scanner 11 will be described in detail with reference to FIG. 6.

Figure 6:
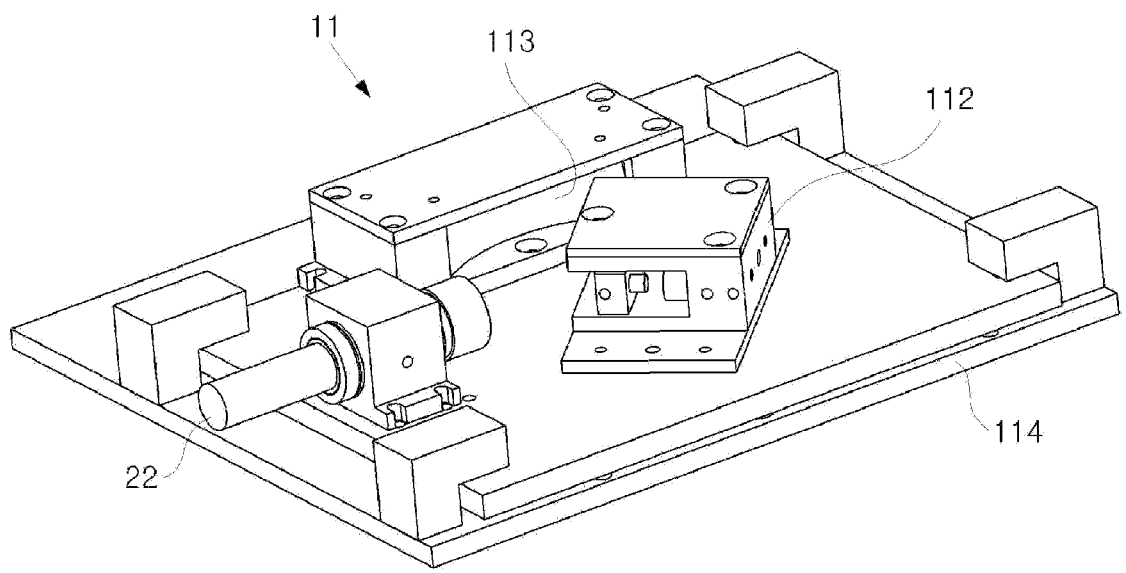
FIG. 6 shows a perspective view of a laser beam scanner.

As shown in FIG. 6, the laser beam scanner 11 includes a laser beam generator 111, a swing mirror 112 for deflecting the laser beams to an fθ lens 113 while swinging to the right and left by applied power, where the fθ lens 113 constantly controls a focal length of the laser beams deflected by the swing mirror 112, and a support plate 114 for fixing the laser beam generator 111, the swing mirror 112, and the fθ lens 113. A fixing means for fixing the laser beam scanner 11 to the side plate 1a can be provided at the side of the support plate 114.

Referring to FIG. 4 again, a case in which two reflection mirrors 12a and 12b are installed is shown. The laser beam output by the laser beam scanner 11 changes its progressing direction on the first reflection mirror 12a and the second reflection mirror 12b and is irradiated to a scanning point 13.

The scanner includes an edge sensor 13a, an optical fiber 13b, and an amplifier 13c, and can further include a fiber guide plate 13d.

The laser beam is swung and irradiated on the image plate 31, and the edge sensor 13a senses the time when the irradiation direction of the laser beam is changed at both end points of the image plate 31. The edge sensor 13a accurately finds which part's signal corresponds to the pixel that corresponds to the 2D image.

The optical fiber 13b collects the light that is excited and generated by the X-rays that are irradiated to the image plate 31 and transmits the light to the amplifier 13c. The optical fiber 13b can be configured with a fiber bundle including a plurality of optical fibers, and in this case, one side of the optical fiber bundle 13b is disposed to be uniformly spread by the width of the image plate 31, and another side thereof is connected as a bundle to the amplifier 13c.

The amplifier 13c transmits light of the wavelength of blue and blocks light of the wavelength of red from among the light collected by the optical fiber 13b by using a band-pass filter (not shown). The amplifier 13c senses intensity of the filtered image signal by using a PMT sensor (not shown), and amplifies it with predetermined intensity.

The optical fiber guide plate 13d securely provides the optical fiber 13b to the amplifier 13c so that the optical fiber 13b disposed as strands may not cover the laser beam.

The image plate transfer device will now be described.

In FIG. 4, the image plate transfer device includes a scan drum 110 for winding the image plate 31, at least one roller 120a-120c installed to be attached to the scan drum 110, an electric power means 130 for supplying driving power to transfer the image plate 31, and a driving power transfer means 140 for transmitting the driving power of the electric power means 130 to the scan drum 110. It is desirable to manufacture the image plate 31 with a material that has a bending characteristic and a restoring characteristic so that the image plate 31 may be wound on the scan drum 110.

The scan drum 110 will be described later.

The rollers 120a-120c support the image plate 31 so that the image plate 31 may be closely wound on the scan drum 110. FIG. 4 shows an example of using three rollers 120a-120c, particularly.

In the example of FIG. 4, a scanning point 13 is provided between the first roller 120a and the second roller 120b, and an eraser 14 is provided between the second roller 120b and the third roller 120c. The eraser 14 is fixed by a prop plate 14a that is installed between the second roller 120b/the third roller 120c and the laser beam scanner.

It is desirable to dispose the second roller 120b and the third roller 120c very close to the top and bottom of the eraser 14 so as to prevent the light emitted by the eraser 14 from influencing the scanning point 13. In another way, a blocking member (not shown) in a U shape can be additionally installed between the second roller 120b and the third roller 120c so as to prevent the light emitted by the eraser 14 from being output to an undesired point.

A DC motor or an AC motor can be used as the electric power means 130, and any one of a stepping motor, a geared motor, and a brushless motor based upon it can be used. When the stepping motor is used, the stepping motor is rotated at a predetermined angle or is inversely rotated according to a pulse signal input to the controller 1000.

A timing belt, a chain, or a gear can be used for the driving power transfer means 140. In FIG. 4, a first belt pulley 110b is combined with a rotation shaft 110a of the scan drum 110, a second belt pulley 130b is combined with a rotation shaft 130a of the electric power means 130, and a timing belt is used to transmit the driving power applied to the second belt pulley 130b to the first belt pulley 110b. Also as shown in FIG. 5, the first belt pulley 110b and the second belt pulley 130b can be disposed outside the side plate 1a.

Finally, the controller 1000 controls the X-ray image capturing device. For example, scanning is performed by controlling the laser beam scanner 11 of the image scanning device and a scanner, and the image plate 31 is reset by controlling the eraser 14. Also, the controller 1000 controls transfer direction and/or transfer speed of the image plate 31 by controlling the electric power means 130 of the image plate transfer device. Further, the controller 1000 provides image information captured by the scanner to the outside.

The scan drum 110 will now be described in detail.

As shown in FIG. 4 and FIG. 5, the scan drum 110 is combined to both side plates 1a by the rotation shaft 110a penetrating the scan drum 110, and a bearing 110e for rotating the scan drum 110 is provided at both ends of the rotation shaft 110a combined with the side plate 1a. A protection cover 110f of the scan drum 110 can be further installed at one outer side of the scan drum 110.

A fastening means for fixing the transfer plate 31 to the scan drum 110 is installed at one surface of the scan drum 110 and one end of the transfer plate 31. The transfer plate 31 fixed by the fastening means is wound on the surface of the scan drum 110 as the scan drum 110 is rotated.

Figure 7:
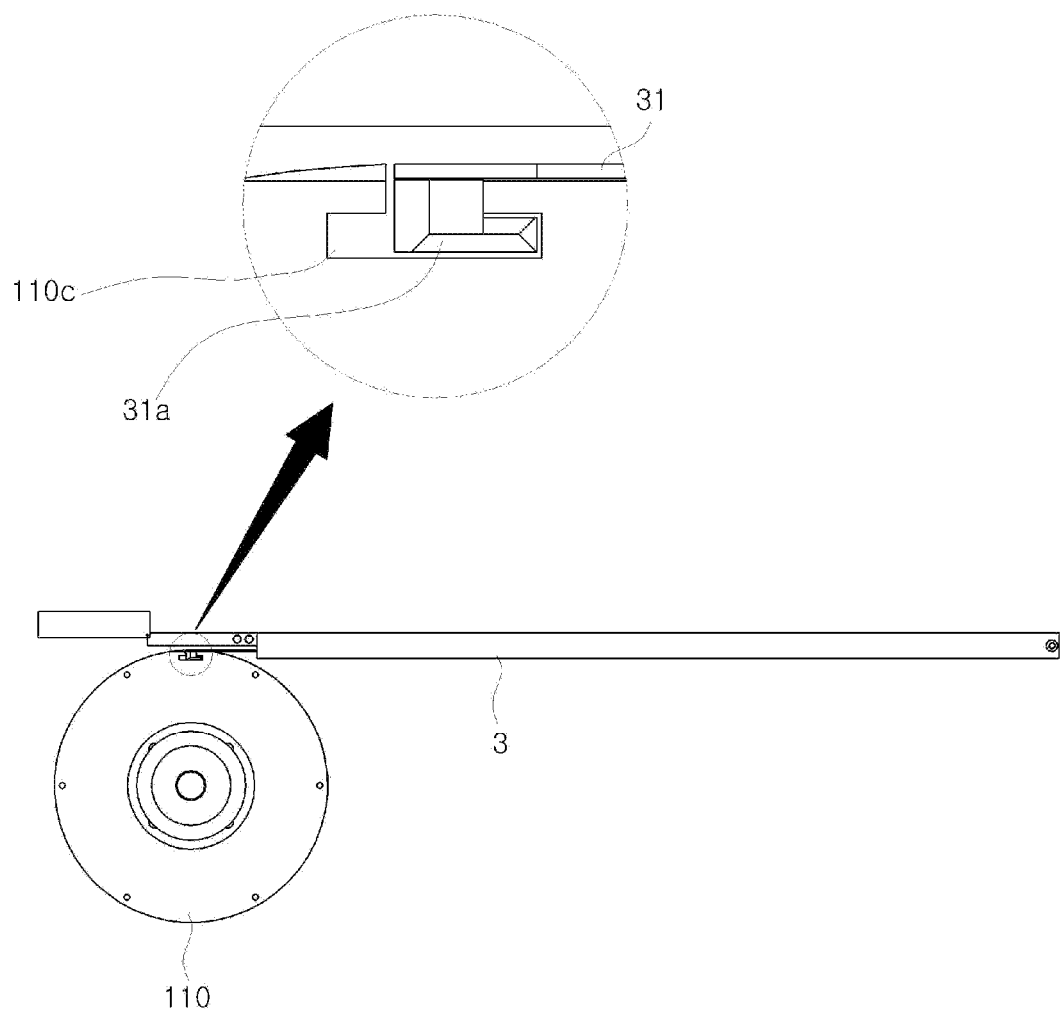
FIG. 7 shows an enlarged view of a state in which a scan drum and a transfer plate are fastened by a latch means.

FIG. 7 shows an enlarged view of a state in which a scan drum 110 and a transfer plate 31 are fastened by a latch means, as an example of the fastening means.

As shown in FIG. 7, the latch means is configured with an L-shape latch protrusion 31a formed at an end of the image plate 31, and a latch groove 110c that is formed in a ⊥ or L shape on the surface of the scan drum 110 so that the latch protrusion 31a may be inserted and fastened.

The image plate transfer device can further include a rotational sensor 150 for sensing the position of the scan drum 110 and/or image plate 31.

Figure 8:
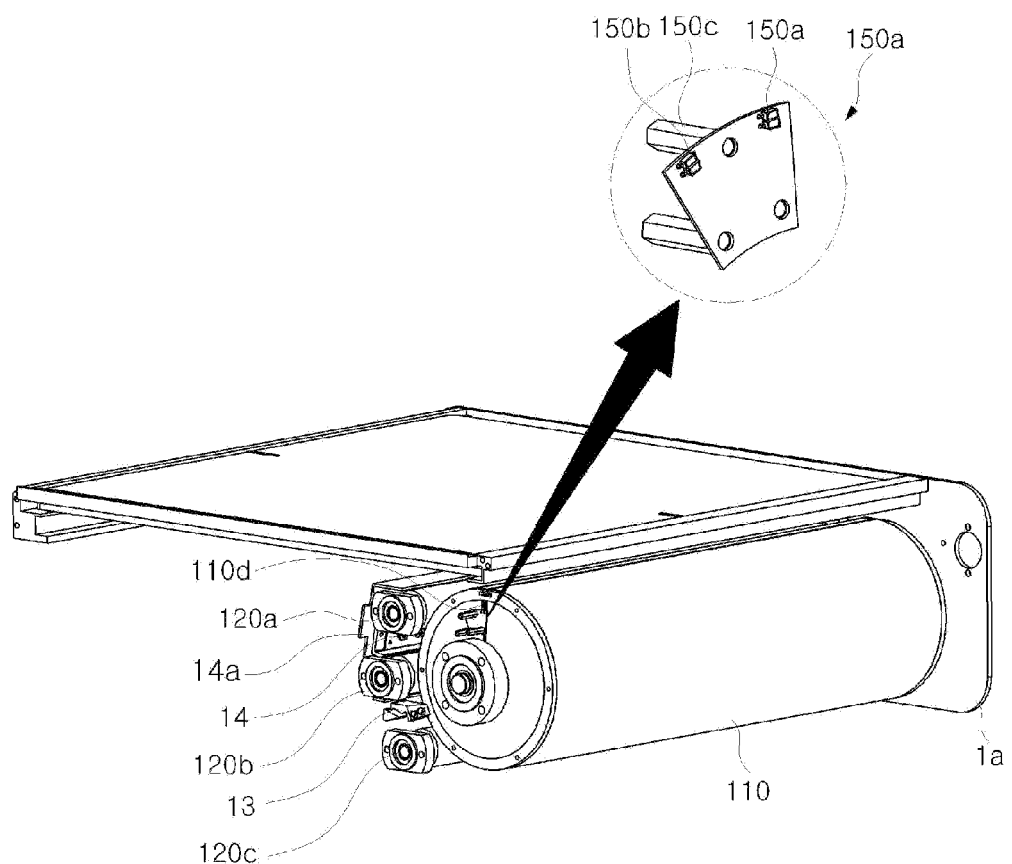
FIG. 8 shows an enlarged view of a rotational sensor.

FIG. 8 shows an enlarged view of a rotational sensor 150 and an installation position thereof. Referring to FIG. 8, the rotational sensor 150 includes an origin sensor 150a for sensing origin position of the scan drum 110 before scanning is started, and a reinsertion sensor 150b for sensing a position of an end of the image plate 31 after the scanning is finished. The rotational sensor 150 can further include three fixing units 150c for fixing the rotational sensor 150 to a predetermined position of the side plate 1a. However, FIG. 8 only shows one example of the rotational sensor 150, and the number and position of the sensor elements 150a and 150b and the fixing units 150c are variable.

When a reflective photo-interrupter is used as the origin sensor 150a and the reinsertion sensor 150b, a position display means 110d can be installed at the side that faces the rotational sensor 150 from among the two sides of the scan drum 110 so that the rotational sensor 150 may easily sense the position of the scan drum 110. When a reflective film is used as an example of the position display means 110c and one side of the scan drum 110 to which the reflective film is attached is processed to be black, the position of the scan drum 110 can be more easily detected because of the reflectance difference between the reflective film and its side. It is desirable to process the one side of the scan drum 110 to be matte.

An operational process of an X-ray image capturing device according to a first exemplary embodiment of the present invention will now be sequentially described.

A cassette 2 is installed in the X-ray image capturing device.

It is desirable for the controller 1000 to control the image plate transfer device so that the scan drum 110 may always stands by at the origin position while the cassette 2 is not installed. The user pushes the cassette 2 into the insert hole 23a at the side of the case main body 1. In this instance, the user pushes the latch protrusion 31a of the image plate 31 built in the cassette 2 into the latch groove 110c of the scan drum 110.

The subject is positioned at the cross point of the front plate 22 and the X-rays are irradiated thereto.

When a scan instruction is input to the image capturing device, the controller 1000 controls the electric power means 130 to quickly transfer the start part of the image plate 31 to the scanning point 13, and controls the electric power means 130 to slowly transfer the other part of the image plate 31 up to its end part for the purpose of acquiring quality scanning. When the end part of the image plate 31 passes through the eraser 14, the controller 1000 controls the electric power means 130 so that the image plate 31 may be quickly transferred until the reinsertion position. Here, the reinsertion position represents the point where the position display means 110c of the scan drum 110 is sensed by the reinsertion sensor 150b.

When a scan instruction is input to the image capturing device, the controller 1000 operates the scanner and the eraser 14 simultaneously. The image plate 31 scans the X-ray latent image while passing through the scanning point 13, and eliminates the X-ray latent image while passing through the eraser 14.

When the end part of the image plate 31 reaches the reinsertion position, the controller 1000 controls the electric power means 130 so that the image plate 31 may be quickly transferred in the opposite direction to reach the initial origin position. The origin sensor 150a notifies whether the image plate 31 has returned to the origin position.

[Mode for Invention]

A second exemplary embodiment discloses an X-ray image capturing device using an up-mounting type of cassette.

When a cassette having a built-in image plate is provided on the X-ray image capturing device, a locking pin installed at both sides of the scan drum is fastened to a locking hole provided at both sides of one end of the image plate. The cassette is referred to as the up-mounting type of cassette.

Figure 9:
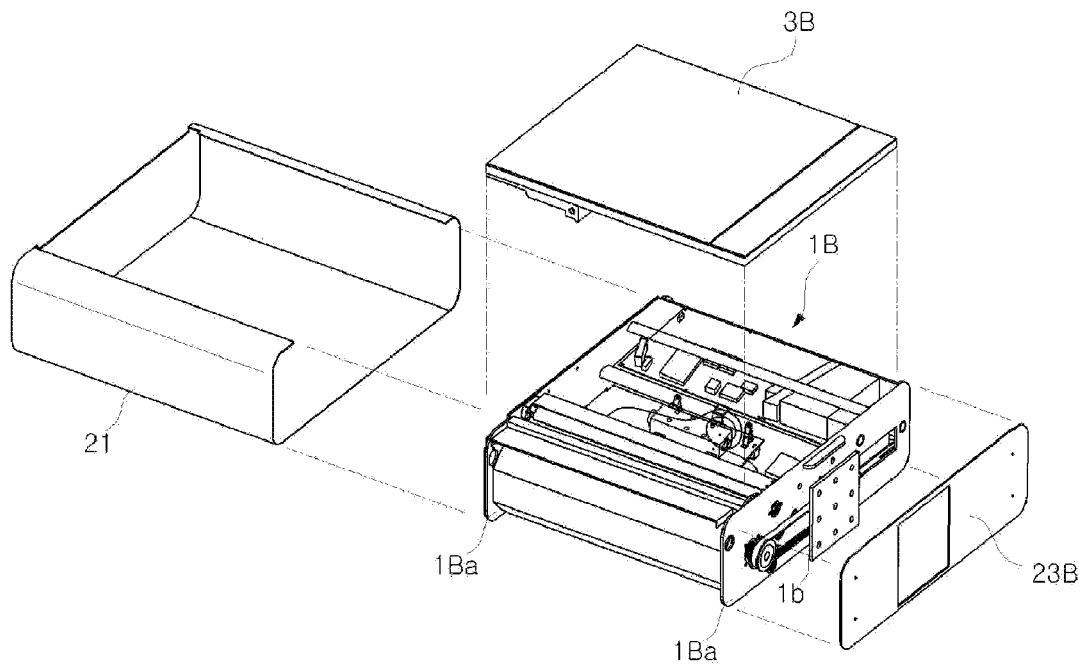
FIG. 9 shows an exploded perspective view of an X-ray image capturing device according to a second exemplary embodiment of the present invention.

FIG. 9 shows an exploded perspective view of an X-ray image capturing device according to a second exemplary embodiment of the present invention.

As shown in FIG. 9, the X-ray image capturing device includes an internal body 1B having an image plate transfer device, an external housing surrounding the internal body 1B, a cassette 3B having an image plate, and a cartridge (not shown) additionally installed in the X-ray image capturing device from the top of the cassette 3B.

The external housing 2B includes a case main body 21, and a side cover 23B for protecting the side of the internal body 1B.

A top side of the cartridge is protected by a front plate (not shown), and an ion chamber (not shown) and a grid (not shown) are installed in the cartridge. The cartridge (not shown) is installed in the top side of the X-ray image capturing device through an installing groove (not shown) or an installing bolt (not shown).

Side plates 1Ba for fixing the image plate transfer device are installed at both sides of the internal body 1B, and an arm mount 1b for fixing the X-ray image capturing device to the X-ray bucky stand or the X-ray bucky table is installed in at least one of the side plates 1Ba. A configuration of the internal body 1B will be described in further detail with reference to FIG. 10.

Figure 10:
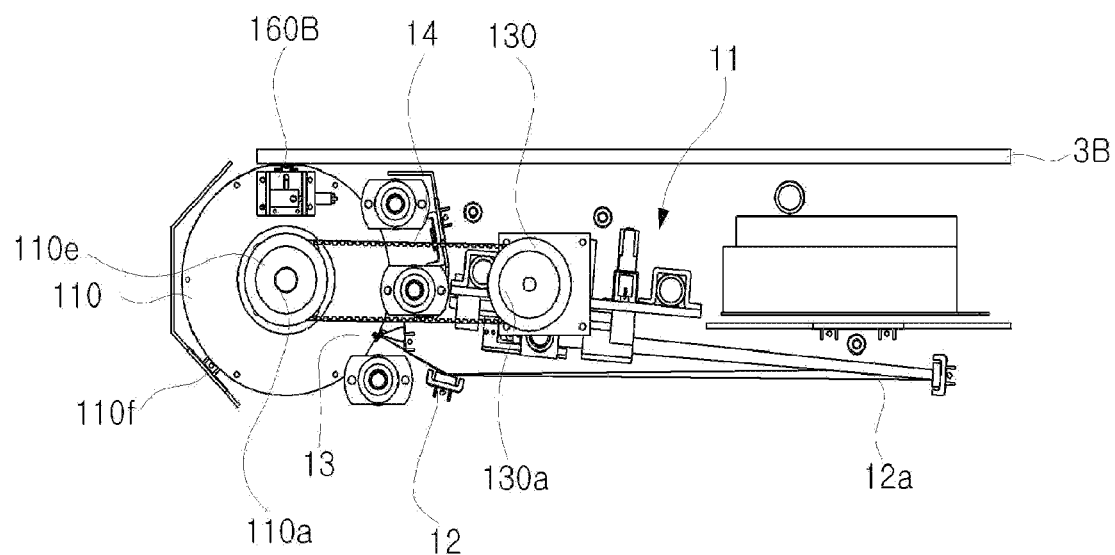
FIG. 10 shows a side view of a state in which a side plate is removed from an internal body of FIG. 9.

FIG. 10 shows a side view of a state in which a side plate 1Ba is removed from an internal body 1B of FIG. 9.

The internal body 1B includes an image scanning device, an image plate transfer device, and a controller 1000B. As shown in FIG. 10, the image scanning device, the image plate transfer device, and the controller 1000B are fixed to the internal body 1B by at least one support plate. A gap between the side plates 1Ba is maintained to be constant by at least one supporter 1Bc disposed in the horizontal direction with respect to the internal body 1B.

First, the image scanning device will be described.

The image scanning device according to the second exemplary embodiment of the present invention corresponds to that of the first exemplary embodiment of the present invention. Therefore, repeated description of the first exemplary embodiment will be omitted, and the reference numerals used for the image scanning device according to the first exemplary embodiment will also be used for the second exemplary embodiment.

Referring to FIG. 10, the image scanning device includes a laser beam scanner 11, at least one or more reflection mirrors 12a-12b for controlling a progressing angle of the laser beam to irradiate the laser beam to a predetermined scanning point 13, and a scanner for scanning an X-ray latent image of the image plate 31B, and it can further include an eraser 14 for eliminating the X-ray latent image by exposing the image plate 31B to strong light.

The image plate transfer device will now be described.

Referring to FIG. 10, the image plate transfer device includes a scan drum 110B for winding the image plate 31B, a lock control assembly 160B for fixing or releasing one end of the image plate 31B to/from the scan drum 110B, at least one or more rollers 120a-120c installed to be attached to the scan drum 110B, an electric power means 130 for supplying driving power for transferring the image plate 31B, and a driving power transfer means 140 for transmitting the driving power of the electric power means 130 to the scan drum 110B. It is desirable to manufacture the image plate 31B built in the cassette 3B with a material that has a bending characteristic and a restoring characteristic so that the image plate 31B may be wound on the scan drum 110B.

The configuration of the image plate transfer device shown in FIG. 10 corresponds to that of the first exemplary embodiment except the scan drum 110B and the lock control assembly 160B. Therefore, a method for installing the image plate 31B of the cassette 3B in the scan drum 100B, and the lock control assembly 160B for automating the method, will now be described.

The configuration of the cassette 3B will now be described.

Figure 11:
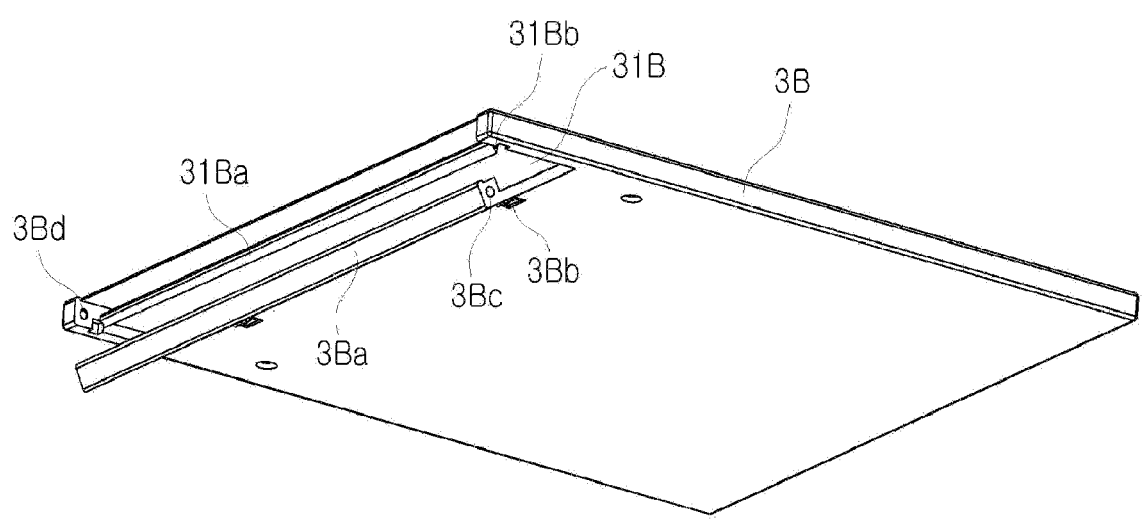
FIG. 11 shows a perspective view of a cassette from bottom to top.

FIG. 11 shows a perspective view of a cassette 3B from bottom to top.

As shown in FIG. 11, an installing protrusion 31Ba to be inserted into the installing groove of the scan drum 100B is formed at one end of the image plate 31B built in the cassette 3B, and a locking hole 31Bb for fixing the installed image plate 31B to the scan drum 100B is formed at both ends of the installing protrusion 31Ba.

A cassette door 3Ba for protecting the image plate 31B at the side where the installing protrusion 31Ba and the locking hole 31Bb are formed can be further included in the cassette 3B.

In the example of FIG. 11, the cassette door 3Ba is combined to the cassette 3B with a hinge 3Bb, and in this case, a part of the outside of the cassette door 3Ba is made of a magnetic material and the outside of the cassette 3B contacting the part of the outside thereof can be made of a magnetic or metal material so that the cassette door 3Ba may be fixed while being opened to the maximum.

Also, a fixing member 3Bc configured with a ball and a spring can be installed at both ends of one side of the cassette door 3Ba so that the cassette door 3Ba may be fixed and shut. A fixing groove 3Bd corresponding to a fixing assembly configured with the ball and the spring is formed at both inner parts of an end of the cassette 3B.

The scan drum 110B will now be described.

Figure 12:
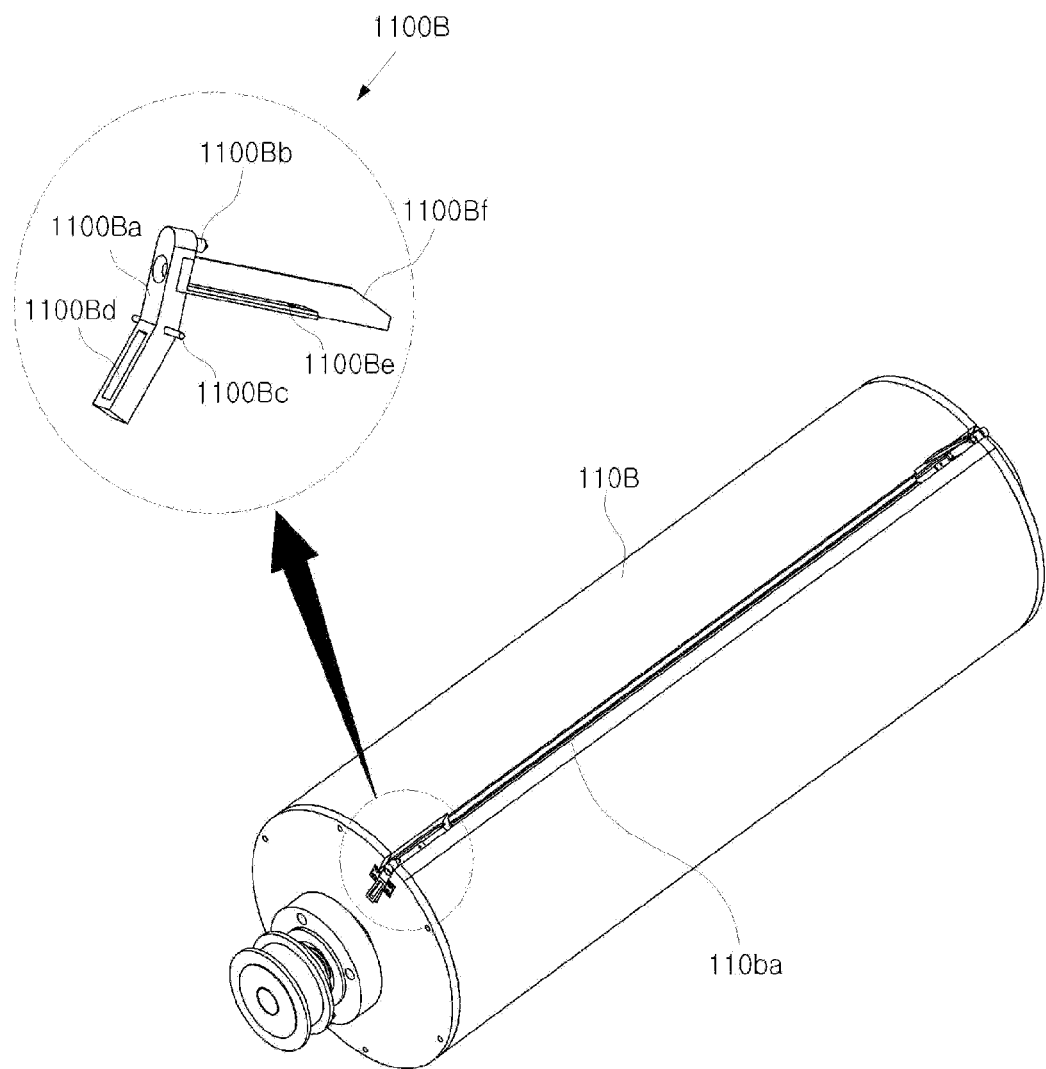
FIG. 12 and FIG. 13 show perspective views of a scan drum in which a locking means is installed.
Figure 13:
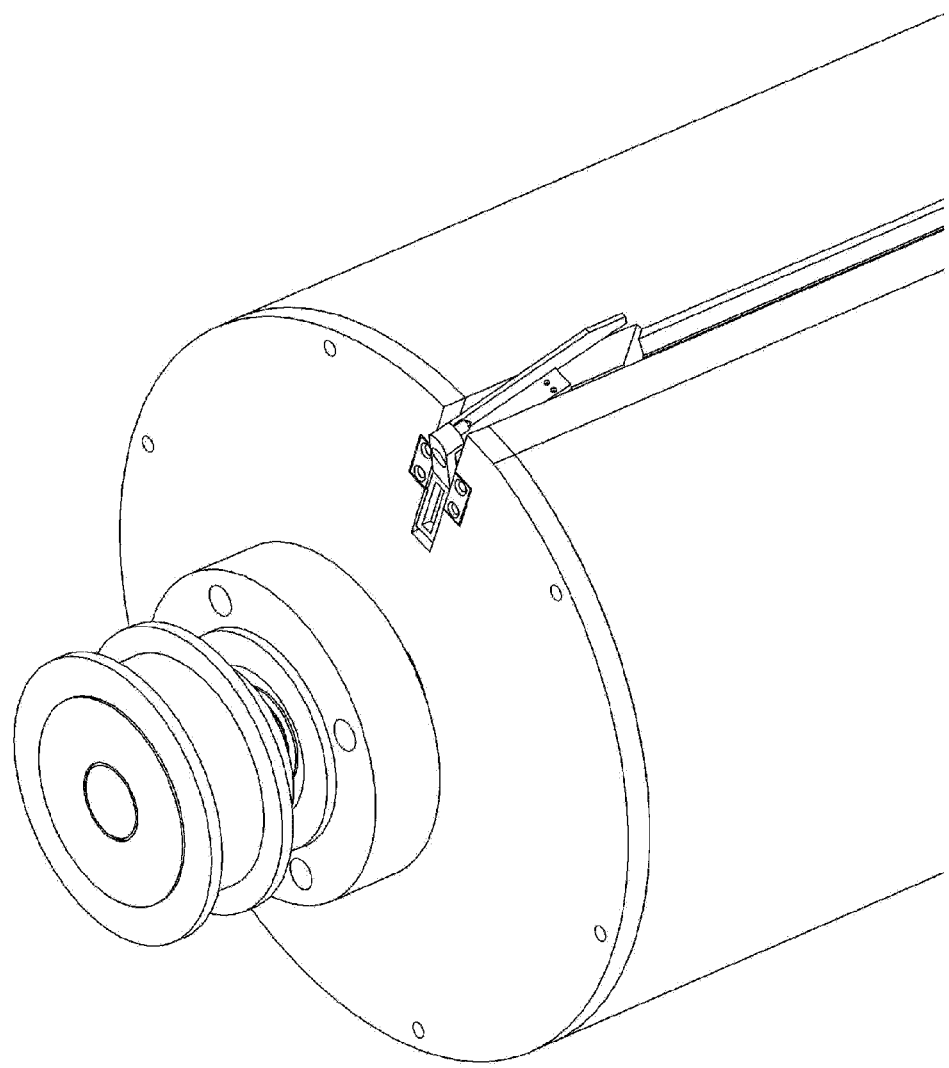

FIG. 12 and FIG. 13 show perspective views of a scan drum 110B in which a locking means 1100B is installed. FIG. 12 shows a locked locking means 1100B, and FIG. 13 shows a released locking means 1100B.

An installing groove 110Ba for inserting an installing protrusion 31Ba of the image plate 13B is formed on a surface of the scan drum 110B. It is desirable to form an end of the installing protrusion 31Ba to be an inverted triangle ∇ and form the installing groove 110Ba to be the shape of a V so as to accurately insert the installing protrusion 31Ba into the center of the installing groove 110Ba.

FIG. 12 shows an enlarged locking means 1100B.

As shown in FIG. 12, the locking means 1100B includes a body 1100Ba having a center part that is bent by a predetermined angle, a locking pin 1100Bb inserted into the locking hole 31Bb of the image plate 13B in the locked state and fixing the image plate 13B to the scan drum 110B, a pivot 1100Bc formed at both sides of the bent part of the body 1100Ba and sustaining the locking means 1100B, and a control groove 1100Bd formed in the groove shape at the bottom of the bent part of the body 1100Ba and switching the locking means 1100B to the locked state or the released state by control of the lock control assembly 160B.

The locking means 1100B may further include a state maintain plate 1100Be attached to the body 1100Ba in the direction of the locking pin 1100Bb, combined at the end by an elastic means (not shown) such as a spring, and maintaining the default state of the locking means 1100B at the locked state, and an attach/detach leading plate 1100Bf formed on the top of the body 1100Ba, vertical to the state maintain plate 1100Be, and pushing the image plate 31B so as to detach the image plate 31B from the installing groove 110Ba of the scan drum 110B in the released state.

In addition, as shown in FIG. 10, the scan drum 110B is combined to both side plates 1Ba by the rotation shaft 110a penetrating the scan drum 110B, and a bearing 110e for fluently rotating the scan drum 110B is installed at both sides of the rotation shaft 110a of the part that is combined with the side plate 1Ba. A protection cover 110f of the scan drum 110B can be further installed in an external side of the scan drum 110B.

The image plate transfer device according to the second exemplary embodiment can further include a scan drum 110B and a rotational sensor 150 for sensing the position of the image plate 31B in a like manner of the first exemplary embodiment. A position display means 110d corresponding to the first exemplary embodiment can be further installed in the scan drum 110B according to the second exemplary embodiment.

The lock control assembly 160B will now be described.

Figure 14:
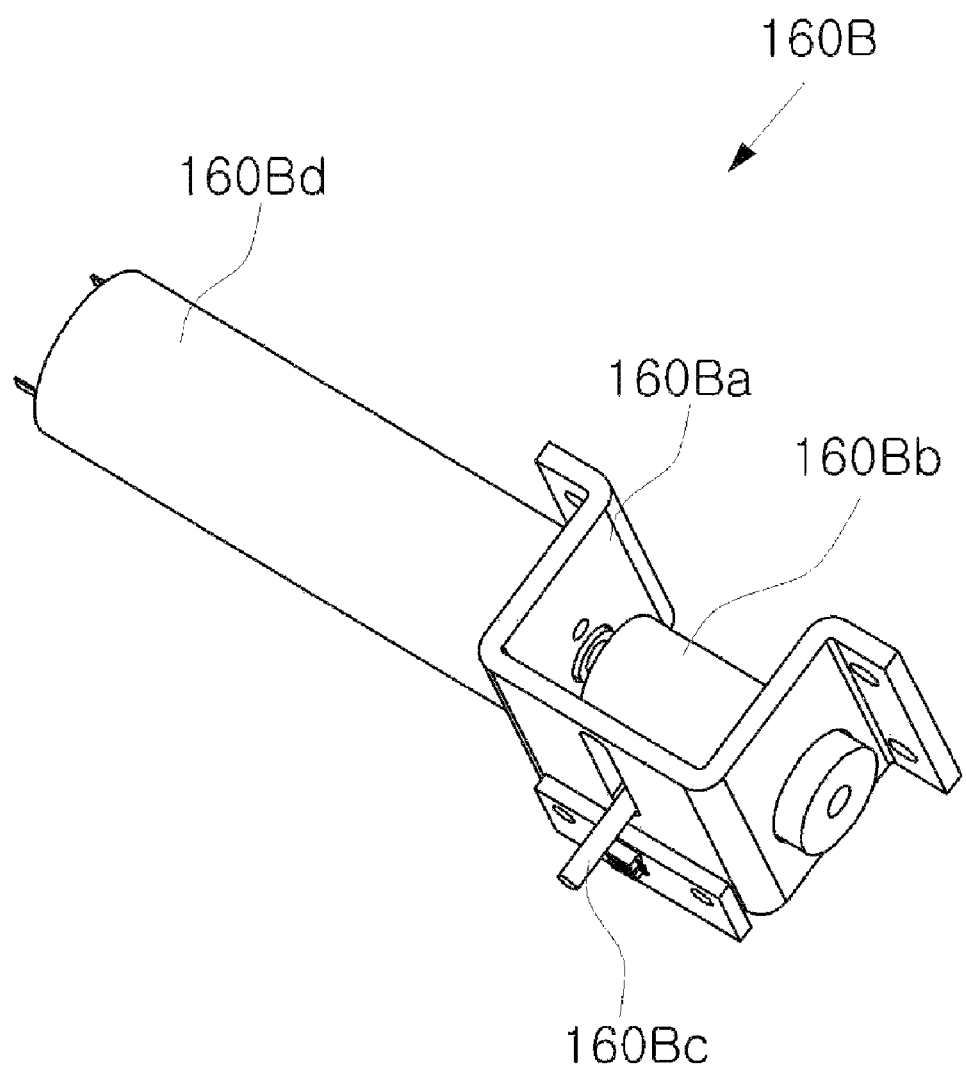
FIG. 14 shows a perspective view of a lock control assembly.

FIG. 14 shows a perspective view of a lock control assembly 160B.

As shown in FIG. 14, the lock control assembly 160B includes a body 160Ba, a drive shaft 160Bb, a state change pin 160Bc, and an electric power means 160Bd.

The state change pin 160Bc is vertically inserted into the control groove 1100Bd of the locking means 1100B by penetrating through a long groove formed from top to bottom in the body 160B, and moves up and down according to rotation/reverse rotation of the drive shaft 160Bb fastened to the rear to switch the locking means 1100B to the locked state or the released state.

A shaft of the electric power means 160Bd is combined with the drive shaft 160Bb in the parallel direction and applies torque or inverse torque to the drive shaft 160Bb. A DC motor or an AC motor can be used for the electric power means 160Bd, and a stepping motor, a geared motor, or a brushless motor using the same can also be used. When a DC geared motor is used, it is rotated or inversely rotated by a predetermined angle according to a pulse signal input to the controller 1000B.

Figure 15:
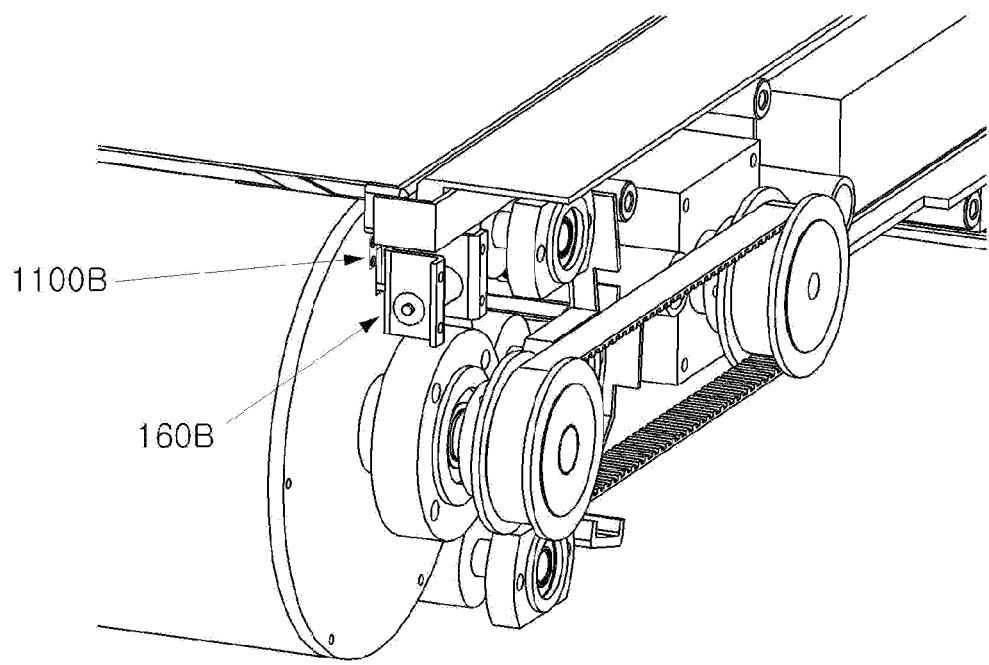
FIG. 15 shows a state in which a state change pin of a lock control assembly is in the released state.
Figure 16:
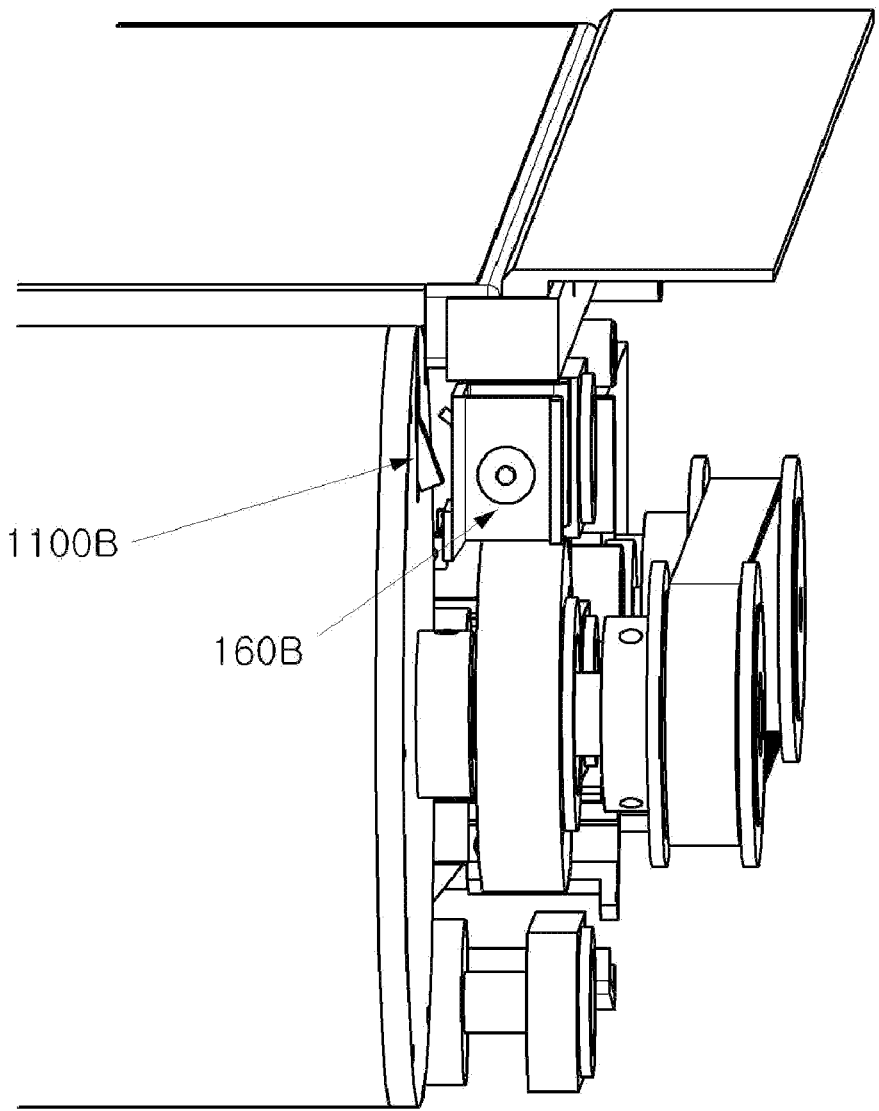
FIG. 16 shows a state in which a state change pin is in the locked state.

FIG. 15 shows a state in which a state change pin 160Bc of a lock control assembly 160B is in the released state, and FIG. 16 shows a state in which a state change pin 160Bc is in the locked state.

As shown in FIG. 15, when a control signal is applied to the electric power means 160Bd, counterclockwise torque is applied to the drive shaft 160Bb, and when the state change pin 160Bc pushes the control groove 1100Bd of the locking means 1100B in the scan drum, the locking pin 1100Bb of the locking means 1100B is separated from the image plate 13B and the attach/detach leading plate 1100Bf of the locking means 1100B simultaneously pushes the image plate 31B from the installing groove 110Ba of the scan drum 110B. Therefore, the image plate 31B of the cassette becomes released.

Also as shown in FIG. 16, when a control signal is applied to the electric power means 160Bd, clockwise torque is applied to the drive shaft 160Bb, and when the state change pin 160Bc accordingly leaves the control groove 1100Bd of the locking means 1100B, the state maintain plate 1100Be returns to the original position by the spring and the locking pin 1100Bb of the locking means 1100B is inserted into the locking hole 31Bb of the image plate 13B. Accordingly, the image plate 31B of the cassette becomes locked.

The controller 1000B functions in a like manner of the controller 1000 of the first exemplary embodiment. Additionally, the controller 1000B controls the electric power means 160Bd of the lock control assembly 160B to switch the image plate 31B of the cassette to the locked state or the released state.

An operational process of the X-ray image capturing device according to the second exemplary embodiment will now be described sequentially.

The cassette 2B is installed in the X-ray image capturing device.

It is desirable for the controller 1000B to control the image plate transfer device to control the scan drum 110B to stand by in the origin position while the cassette 2B is not installed. The user opens the cassette door 3Ba and adheres the cassette 2B to the top surface of the X-ray image capturing device. In this instance, the installing protrusion 31Ba of the image plate 31B built in the cassette 2B is inserted into the installing groove 110Ba of the scan drum 110B.

When receiving a cassette installing instruction from the user, the controller 1000B controls the lock control assembly 160B to insert the locking pin 1100Bb of the locking means 1100B into the locking hole 31Bb of the image plate 13B. The image plate 31B of the cassette resultantly becomes locked.

A sensor (not shown) for recognizing insertion of the installing groove 110Ba into the image plate 31B can be further installed in a part of the scan drum 110B. In this case, upon recognizing insertion of the image plate 31B through the sensor, the controller 1000B automatically controls the lock control assembly 160B to lock the image plate 31B.

The subsequent operational processes correspond to those of the first exemplary embodiment.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

[Industrial Applicability]

The present invention relates to a compact digital X-ray image capturing device for convenient mobility.

The invention claimed is:

1. A digital X-ray image capturing device comprising:
  a cassette having a built-in image plate;
  an image plate transfer device for taking the image plate out of the cassette and transferring the same to a scanning point;
  an image scanning device for scanning an X-ray latent image of the image plate by irradiating laser beams to the scanning point;
  an internal body including the image plate transfer device and the image scanning device; and
  an external housing surrounding the internal body.

2. The digital X-ray image capturing device of claim 1, wherein the image plate transfer device includes:
  a scan drum having a fastening means on a surface, the fastening means being combined with an end of the image plate;
  at least one roller installed near the scan drum to closely wind the image plate on the surface of the scan drum; and
  an electric power means for applying torque to the scan drum.

3. The digital X-ray image capturing device of claim 2, wherein
  the fastening means formed on a surface of the scan drum is a latch groove, and
  a latch protrusion formed at an end of the image plate is combined with the latch groove.

4. The digital X-ray image capturing device of claim 3, wherein
  the latch groove is formed in one of the shapes ⊥ and L, and
  the latch protrusion is formed in one of the shapes ⊥ and L.

5. The digital X-ray image capturing device of claim 3, wherein
  an inserting groove for installing the cassette in the image plate transfer device is formed on the top of a side of the external housing.

6. The digital X-ray image capturing device of claim 2, wherein
  the fastening means formed on a surface of the scan drum is an installing groove, and
  an installing protrusion formed at an end of the image plate is combined with the installing groove.

7. The digital X-ray image capturing device of claim 6, wherein
  a locking hole for fixing an end of the image plate to a surface of the scan drum is formed at both sides of the end of the image plate.

8. The digital X-ray image capturing device of claim 7, wherein the scan drum further includes
  a locking means including a locking pin, inserted into the locking hole of the image plate, for fixing the image plate to the scan drum.

9. The digital X-ray image capturing device of claim 8, wherein the locking means includes:
  a body a center point of which is bent by a predetermined angle;
  a pivot formed at both sides of the body and rotatable by the angle that the body is bent; and
  a control groove, formed as a groove at the bottom of the bent point, for controlling rotation of the body.

10. The digital X-ray image capturing device of claim 9, wherein the locking means further includes
  a state maintain plate, attached to the body in the locking pin direction, having an end to which an elastic means for applying elastic force to the control groove is adhered so as to insert the locking pin into the locking hole of the image plate.

11. The digital X-ray image capturing device of claim 9, wherein the image plate transfer device further includes a lock control assembly including a body, a drive shaft, and a state change pin, and
  the state change pin is vertically inserted into a control groove of the locking means by penetrating a groove formed in the body from top to bottom, and it moves up and down according to rotation and reverse rotation of the drive shaft fastened to an end and controls the locking pin of the locking means.

12. The digital X-ray image capturing device of claim 7, wherein the cassette further includes
  a cassette door for protecting an end of the image plate fastened to the scan drum.

13. The digital X-ray image capturing device of claim 2, wherein the image plate transfer device further includes
  a driving power transfer means for transferring torque of the electric power means to the scan drum.

14. The digital X-ray image capturing device of claim 13, wherein
  the driving power transfer means is a timing belt, and
  the timing belt connects a first belt pulley installed at a rotation shaft of the scan drum and a second belt pulley installed at a shaft of the electric power means.

15. The digital X-ray image capturing device of claim 2, wherein the image plate transfer device further includes
  a rotational sensor for sensing rotational position of the scan drum.

16. The digital X-ray image capturing device of claim 15, wherein
  the sensor includes an origin sensor for sensing an origin position before the scan drum is scanned and a reinsertion sensor for sensing an end position of the image plate after the image plate is scanned.

17. The digital X-ray image capturing device of claim 16, wherein
  a position display means of the scan drum made of a reflective film is attached to a side of the scan drum.

18. The digital X-ray image capturing device of claim 17, wherein
  the one side of the scan drum to which the position display means is attached is rendered to be matt black.

19. The digital X-ray image capturing device of claim 2, wherein the image scanning device includes:
  a scanner for scanning an X-ray latent image of the image plate generated by the laser beams at a scanning point; and an eraser for eliminating the X-ray latent image by irradiating strong light to the image plate.

20. The digital X-ray image capturing device of claim 19, wherein the roller includes a first roller that is disposed in parallel to a rotation shaft of the scan drum, and the scanning point is disposed to one of the top and the bottom of the first roller, and the eraser is disposed at the opposite position of the scanning point with respect to the first roller.

\* \* \* \* \*